United States Patent [19]

Ohashi et al.

[11] Patent Number: 5,139,939
[45] Date of Patent: Aug. 18, 1992

[54] PROCESS FOR THE PRODUCTION OF HUMAN TISSUE PLASMINOGEN ACTIVATOR AND CELL STRAIN USEFUL THEREFOR

[75] Inventors: Akira Ohashi, Yokohama; Yoshitaka Hamaguchi; Nichinori Miyahara, both of Odawara; Yoshio Oyama, Kanagawa; Toru Shiomichi, Odawara, all of Japan

[73] Assignee: Meiji Milk Products Co., Ltd., Tokyo, Japan

[21] Appl. No.: 219,364

[22] Filed: Jul. 15, 1988

[30] Foreign Application Priority Data

Jul. 21, 1987 [JP] Japan ............................... 62-182000

[51] Int. Cl.$^5$ ............................................. C12P 21/02
[52] U.S. Cl. ................................. 435/70.1; 435/240.2; 435/69.2
[58] Field of Search .................... 435/70.1, 70.3, 240.2, 435/69.2

[56] References Cited

U.S. PATENT DOCUMENTS 4,757,005 7/1988 Chan .............................. 435/240.2

OTHER PUBLICATIONS

Chemical Abstracts, vol. 104, No. 17, Apr. 1986, p. 548, Abstract No. 147145a, Columbus, Ohio, US; & JP-A-60 231 611 (Meiji Jilk Products Co., . . .
Chemical Abstracts, vol. 108, No. 11, Mar. 1988, p. 534, Abstract No. 93083r, Columbus, Ohio, US; & JP-A-62 158 219 (Meiji Milk Products Co., . . .
Matsuo et al. Chem. Abstracts vol. 102 1985 Abstract #76954j.
Sekiguchi et al. Biomedicine & Pharmaco Therapy 1985 39, 372-380.

Primary Examiner—David M. Naff
Assistant Examiner—Jane A. Williams
Attorney, Agent, or Firm—Oblon, Spivak, McClelland, Maier & Neustadt

[57] ABSTRACT

Human tissue plasminogen activator is produced by culturing a human rhabdomyosarcoma-derived cell, KYM-SF, in a medium, followed by purification of single-chain and/or double-chain human tissue plasminogen activator from the medium.

2 Claims, 3 Drawing Sheets

PROCESS FOR THE PRODUCTION OF HUMAN TISSUE PLASMINOGEN ACTIVATOR AND CELL STRAIN USEFUL THEREFOR

BACKGROUND OF THE INVENTION

1. Field of the Invention

The present invention relates to a process for the production of human tissue plasminogen activator capable of activating plasminogen and also to a human rhabdomyosarcoma-derived cell strain, KYM-SF, useful for the process.

2. Description of the Related Art

Human tissue plasminogen activator is a proteolytic enzyme which is produced by endothelial cells or the like and has high affinity to fibrin contained in aggregates of coagulated blood (thrombi). It serves to activate and convert plasminogen, an inactive proenzyme, into plasmin, a thrombolytic enzyme.

Plasmin which has been produced in circulating blood binds plasmin inhibitor in the blood and is inactivated promptly. Human tissue plasminogen activator (will hereinafter be called "t-PA"), which binds fibrin in thrombi and activates plasminogen there to dissolve the thrombi, has higher specificity to the sites of thrombi than protein therapeutic agents presently available on the market, i.e., urokinase and streptokinase. Therefore, a great deal of development work is now under way on t-PA as a thrombolytic agent which may substitute for such protein therapeutic agents.

Many reports have heretofore been presented with a view toward realizing commercial production of t-PA. Developments have been attained in both techniques making use of genetic engineering and cell culture using human-derived cells. Normal cells such as human endothelial cells and human uterine cells as well as tumor cells such as human melanoma have been known as human-derived-t-PA producing cells [Rijken et al., J. Biol. Chem., 256, 7035-7041 (1981); Vetterlein et al., J. Biol. Chem., 255, 3665-3672 (1980); Wilson et al., Cancer Research, 40, 933-938 (1980)].

A number of reports have heretofore been made on the production of substances using cell culture techniques, in which established cell lines derived from normal cells or tumor cells were adopted. This also applied to the production of t-PA as appeared in the publication of many reports (Japanese Patent Application Laid-Open Nos. 28009/1982; 110625/1984; 19486/1986; 158116/1985; 158117/1985; and 259187/1985).

On the other hand, there are some reports of clinical trials on the in vivo efficacy of t-PA obtained from animal cells manipulated by genetic recombinant techniques. [F. van der Werf et al., N. Eng. Med., 310, 609-613 (1984); The TIMI study group N. Eng. Med., 312(14), 932-936 (1985); D. Collen et al., Circulation, 73(3), 511-517 (1986)]. The results of these clinical trials demonstrated the effectiveness of t-PA but also indicated a problem that massive administration would be indispensable for allowing t-PA to act effectively [D. O. Williams et al., Circulation, 73(2), 338-346 (1986)].

As a result of the development of t-PA, it has now been considered that its effectiveness as a thrombolytic agent can be influenced by the t-PA structures as represented by the single chain or double-chain molecule. Although the structure-activity relationship of tPA has not been fully elucidated, it is considered on the basis of reports published to date that double-chain t-PA has stronger thrombolytic ability but single-chain t-PA is superior as a thrombolytic agent in view of its in vivo stability (resistance to the action of in vivo inhibitors), its higher affinity to fibrin, etc. [E. D. Sprenger et al., Blood, 69(2), 381-387 (1987); Japanese Patent Application Laid-Open No. 118717/1984].

However, the development of t-PA has heretofore been proceeded with centering around double-chain t-PA for the fact that the structure-activity relationship has not been taken into due consideration and also for the following convenience in production. Namely, cell culture making use of a serum-added medium has been needed for the production of t-PA because host cells for recombinant manipulation and established cell lines, both of which have serum requirement, are used as starting materials for its production. In the absence of protease inhibitor, such as aprotinin or the like, it was hence impossible to avoid the conversion of single-chain t-PA, which was converted by proteolytic enzymes contained in serum components, into double-chain t-PA.

The use of serum is however accompanied by problems which should be solved for commercial production.

Namely, serum is costly and accounts for a high percentage of the cost for raw materials in the culture step. It is also necessary to remove serum-derived substances (contaminating proteins, endotoxins, mycoplasmas, virus, etc.) in order to purify a substance produced by cells and to formulate it for application as a medicine or the like. As far as the production of t-PA is concerned, it has been suggested that t-PA degrading proteases and t-PA specific inhibitors present in serum affect the productivity of t-PA [E. D. Sprenger et al., Blood, 36(2), 381-387 (1987)]. Their removal is also indispensable.

As another effect which may be given on the production of t-PA by the use of serum for cell culture, it is mentioned that the conversion of produced t-PA into double-chain t-PA under the action of certain serum-derived proteases is unavoidable. This effect is certainly associated with the problems mentioned above. It is thus required for the production of single-chain t-PA to conduct the culture in a medium supplemented with an expensive inhibitory protein (aprotinin or the like) [Japanese Patent Application Laid-Open No. 158116/1985] or a costly inhibitor [Japanese Patent Application Laid-Open No. 4233/1987]. Such an additive should be eliminated from a medicine to be formulated [Yakumu Koho, 1271, 17 (Aug. 11, 1984)]. Complex steps are however required to achieve this.

It has hence been desired to develop a technique which promises more economical and efficient production of t-PA using cell culture techniques, no matter whether the cell is produced by genetic recombination or by an established cell line or the like.

There has been a delay, especially, in the development of a technique for efficiently producing single-chain t-PA. Its development has thus been desired strongly, along with a technique for its mass production.

As a promising technique to improve productivity and to gain substantial advantages, serum-free culture of animal cells has been desired for the production of t-PA.

In the course of an investigation on various t-PA producing cells, the present inventors have already isolated a t-PA producing cell strain (IFO 50030; will hereinafter be called "KYM-A") in a clone of KYM-1 isolated from human rhabdomyosarcoma (given kindly by Dr. Morimasa Sekiguchi, The Institute of Medical Science, The University of Tokyo; IFO 50085) as disclosed in Japanese Patent Application Laid-Open No. 1382/1986. A Japanese patent application (now Japanese Patent Application Laid-Open No. 158115/1985) has been filed on a production process of t-PA, which makes use of KYM-A.

Since serum is required for the culture of KYM-A, the above process is an effective production process for double-chain t-PA alone, but not for single-chain and/or double-chain t-PA, however. Due to the use of serum, a great deal of effort has been required in order to overcome such drawbacks.

SUMMARY OF THE INVENTION

The present inventors hence repeated cloning of KYM-A with a view toward finding out a cell strain high in added commercial value. As a result, the present inventors found the human rhabdomyosarcoma variant KYM-SF (IFO 50135; will hereinafter be called "KYM-SF"), which can be subjected to suspension culture with stirring in a serum-free medium and can be subcultured without limitations. The variant was thus established as an established cell line.

It has also been found that use of KYM-SF permits mass production of t-PA and also selective and efficient production of single-chain or double-chain t-PA.

The present invention has been completed based on the above-described findings. A first object of this invention is therefore to provide a process for the production of t-PA.

A second object of this invention is to provide the novel cell strain, KYM-SF, derived from human rhabdomyosarcoma, which is useful in the practice of process described above.

In one aspect of this invention, there is thus provided a process for the production of human tissue plasminogen activator, which comprises culturing a human rhabdomyosarcoma-derived cell, KYM-SF, in a medium and purification of single-chain and/or double-chain human tissue plasminogen activator from the medium.

In another aspect of this invention, there is also provided a cell strain, KYM-SF, having the following characteristic properties:

(1) KYM-SF is a variant derived from human rhabdomyosarcoma-derived cell strain, KYM-A.

(2) Although KYM-SF has both suspension-type and adhesive-type properties in culture, the adhesive-type property is weak and the suspension-type property becomes dominant when it is cultured with stirring.

(3) KYM-SF grows well in suspension culture with stirring and can be subcultured.

(4) The cell shape is highly-refrangible spherical. Adhered cells are also spherical in shape, and chain-like aggregates are also observed.

(5) Its dependency on serum for growth is extremely weak. It grows well in RPMI 1640 medium containing human transferrin, monoethanolamine and selenious acid or in RPMI 1640 medium containing bovine serum albumin of low concentration, human transferrin, monoethanolamine and selenious acid. Subculture can be performed without limitations.

(6) Optimum temperature for its growth is 36° C.-38° C.

(7) Doubling time is approximately 36 hours in a logarithmic growth phase in RPMI 1640 medium which contains human transferrin, monoethanolamine and selenious acid.

(8) KYM-SF cell can be easily preserved at −80° C. for a reasonably long period.

(9) KYM-SF produces human tissue plasminogen activator in a substantial quantity.

According to the present invention, single-chain and/or double-chain t-PA can be produced efficiently by culturing KYM-SF in a medium and then purifying resultant single-chain and/or double-chain t-PA from the medium.

BRIEF DESCRIPTION OF THE DRAWINGS

The above and other objects, features and advantages of the present invention will become apparent from the following description of the invention and the appended claims, taken in conjunction with the accompanying drawings, in which:

DETAILED DESCRIPTION OF THE INVENTION AND PREFERRED EMBODIMENTS

KYM-SF, which is used in this invention, is a variant obtained as a result of cloning of KYM-A at the level of cells. Distinct differences are observed in biological properties between KYM-SF and KYM-A. Namely, KYM-SF produces t-PA in a quantity at least equal to KYM-A and has a property permitting serum-free culture in contrast to KYM-A which requires serum for its growth. Significant differences are hence observed in their growth characteristics.

Described specifically, KYM-SF was obtained by the following cloning procedure.

Fetal bovine serum was added at suitable 8-stage concentrations in the range of 0%–5% respectively to RPMI 1640 medium containing human transferrin (1 $\mu$g/ml), monoethanolamine ($5 \times 10^{-6}$ M) and selenious acid ($1 \times 10^{-8}$ M) (the medium added with the three components will hereinafter be called "TES-RPMI 1640"). The media thus prepared were placed separately in the wells of a 96-well plate. KYM-A cells were inoculated in the wells and cultured for 2 weeks in 5% $CO_2$-containing air at 37° C. while one half of each medium was replaced by the corresponding fresh medium on every third days. The clone of the colony which had grown in the medium of the lowest serum concentration among those produced colonies was transferred to a 24-well plate. The clone which gave the greatest t-PA production was then selected. Using the thus-selected clone and TES-RPMI 1640 containing 0.1% of fetal bovine serum, clones which grew in a suspended state were solely subcultured for about 2 months. Two months later, the clone was inoculated to a 96-well plate, the wells of which were filled separately with media which had been prepared by adding fetal bovine serum to TES-RPMI 1640 at suitable 4-stage concentrations in the range of 0%-0.001% respectively. Under similar culture conditions as for the first selection, the clone was cultured for 2 weeks while replacing one half of each medium with the corresponding fresh medium on every third days. The clone of the colony which had grown in the medium of the lowest serum concentration among those produced colonies was transferred to a 24-well plate. The clone which gave the greatest t-PA production was then selected. Using the thus-selected clone and TES-RPMI 1640 without serum, clones which grew in a suspended state were solely subcultured for about 4 months under serum-free conditions, so that the clone was screened and KYM-SF was obtained successfully.

The serum-independent growth of KYM-SF according to this invention is apparent from a growth curve (FIG. 1) which was obtained by inoculating KYM-SF at an inoculum size of $5\times10^4$ cells/ml in TES-RPMI 1640 without serum on a 24-well plate and then culturing it for 10 days.

Figure 1:
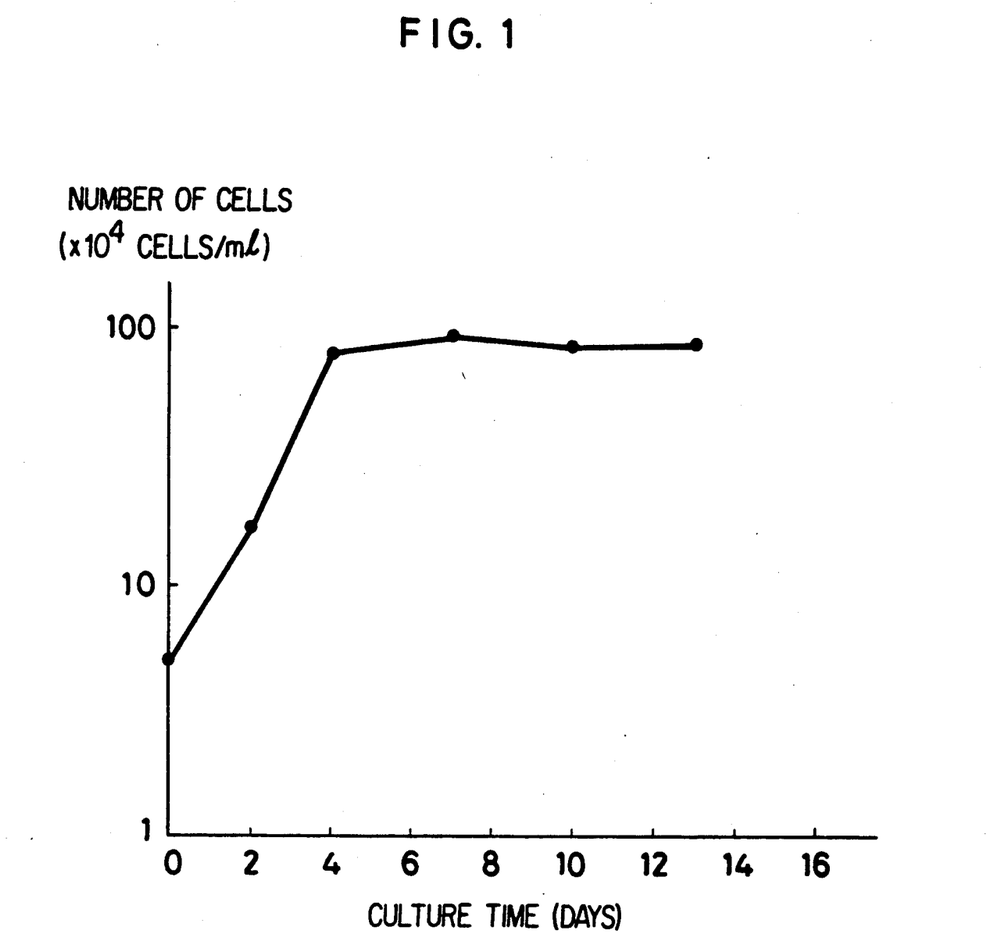
FIG. 1 shows a growth curve of KYM-SF in a serum-free medium.

According to the results shown in FIG. 1, it is envisaged that KYM-SF was satisfactory in both the speed of growth (doubling time: about 36 hours) and the cell density obtained at saturation.

Biological properties of KYM-SF thus isolated may be summarized as follows:

(1) KYM-SF is a variant derived from human rhabdomyosarcoma.

(2) Although KYM-SF has both suspension-type and adhesive-type properties, the adhesive-type property is weak and when cultured with stirring, KYM-SF shows the suspension-type property.

(3) KYM-SF grows well in suspension culture with stirring and can be subcultured.

(4) The cell is highly-refrangible spherical in shape. Adhered cells are also spherical, and chain-like aggregates are often observed.

(5) The serum dependency is extremely weak. KYM-SF grows well in a medium of TES-RPMI 1640 in the presence or absence of bovine serum albumin at a low concentration. Subculture is feasible without limitations.

(6) Optimum temperature for cell growth: 36° C.-38° C.

(7) Doubling time: About 36 hours in a logarithmic growth phase in TES-RPMI 1640.

(8) Cryopreservation: Long-term preservation is feasible at −80° C. with extreme ease.

(9) KYM-SF produces human tissue plasminogen activator in a substantial quantity.

A description will next be made of a process for culturing the above KYM-SF and collecting t-PA.

The culture of KYM-SF is first effected as seed culture in a Petri dish. When the number of cells has reached a suitable value, the culture is transferred to a spinner flask or fermenter to perform suspension culture with stirring there.

The inoculum size may preferably be about $2-5\times10^5$ cells/ml. Subculturing of cells is performed when they reach a stationary phase of growth.

In the process of this invention, it is advantageous to choose a medium most effective from the economical standpoint in light of the properties of KYM-SF so long as no adverse effects are given to its growth. A serum-free medium composed of a basal medium and some additive components is suitable as such a medium.

As the basal medium to be used, RPMI 1640 medium or a 1:1 mixture of RPMI 1640 medium and F12 medium is suitable. These media are generally sold on the market and are readily available. The basal medium is however not necessarily limited to the above-exemplified ones, and any media prepared in accordance with the formulations of the above media may also be used.

As additive components, human transferrin, monoethanolamine and selenious acid are suitable. More preferably, it is desired to add bovine serum albumin to these additive components.

In order to achieve stable subculture in particular, it is most suitable to use RPMI 1640 medium which contains bovine serum albumin, human transferrin, ethanolamine and selenious acid.

It is preferable to add human transferrin at 0.5–1.5 $\mu$g/ml, monoethanolamine at 3–8 $\mu$M and selenious acid at $1\times10^{-7}-1\times10^{-9}$ M, approximately. When bovine serum albumin is used, its addition in concentrations of 0.05–0.3% (w/v) is suitable.

These requirements for a medium are inherent to KYM-SF and have been chosen as giving best economical effects. Needless to say, media obtained respectively by adding serum to the above-described basal media can also be used.

Although no strict limitations are imposed on the conditions for culture, the culture temperature may suitably be 37±1° C. and as a gaseous phase, it is suitable to use air which contains about 5% of $CO_2$. Other conditions for culture in Petri dishes and the like can be fulfilled by replacing the medium at suitable intervals.

For mass culture, these culture conditions become somewhat stricter. As requirements other than those mentioned above, it is preferable to control the pH and dissolved oxygen level. Regarding these additional requirements, it is necessary to prepare a medium in such a way that the pH will remain within 6.5–7.5 and the dissolved oxygen ratio (which means the ratio of dissolved oxygen to the content of oxygen dissolved at saturation and will hereinafter be abbreviated as "$pO_2$") will be at least 10%. These requirements are generally achieved by aerating the medium, but are dependent heavily on a culture apparatus. They are thus attained by using control equipment or the like in combination. These requirements may also be achieved by a method such as suitable medium replacement, medium circulation or continuous medium feeding.

Usually, all t-PA molecules have a single-chain structure at the time of their secretion from cells. It is thus determined by environmental factors, which surround t-PA thereafter, whether tPA retains the single-chain structure or is converted into the double-chain structure. The existence or non-existence of serum-derived proteolytic enzymes controls the environmental factors in many instances.

Incidentally, the term "double-chain structure" as used herein means a structure that the single-chain structure has been cleaved at a certain specific site of its protein portion. It may include the t-PA's structure in which the cleaved peptides are bound by disulfide bonds, apparently showing the single-chain structure under non-reducing conditions on electrophoresis.

Figure 2:
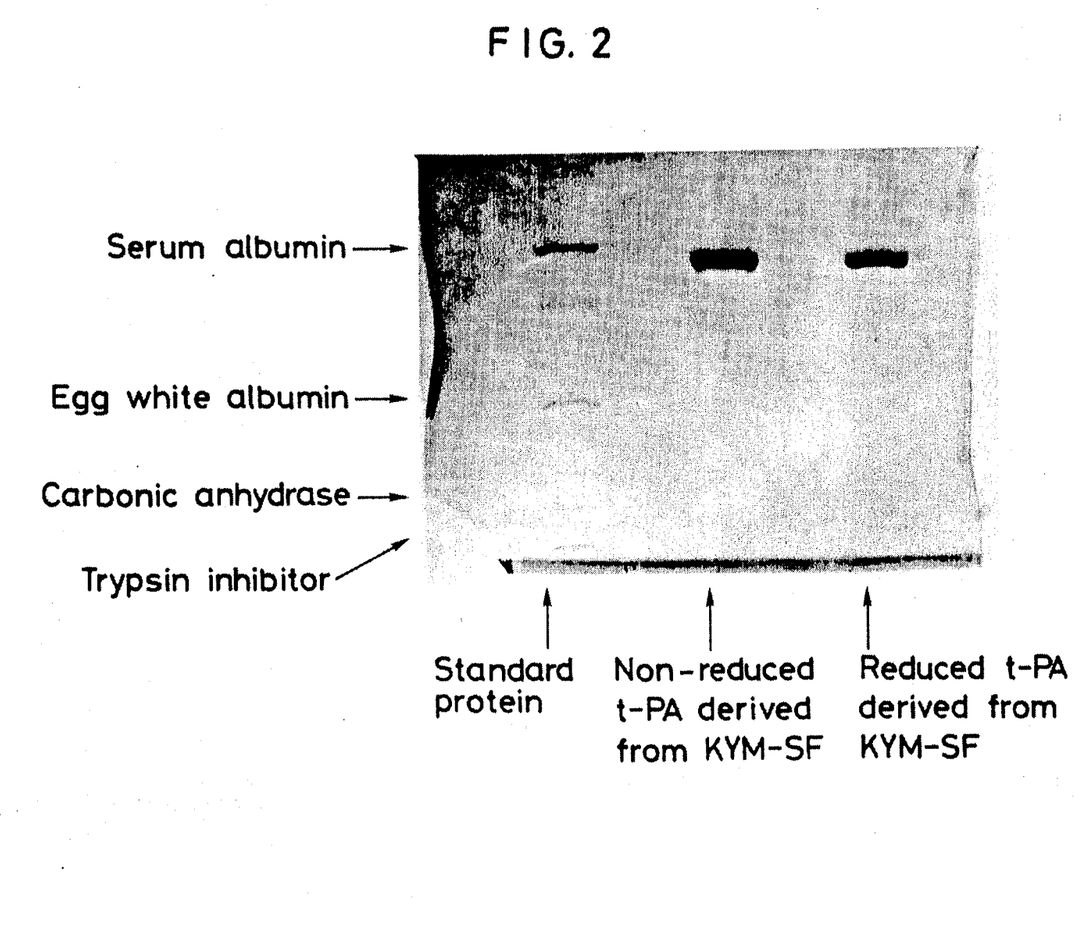
FIG. 2 illustrates results of electrophoresis of t-PA which had been collected and purified from serum-free culture of KYM-SF, in an SDS-polyacrylamide gel under reducing conditions. Standard proteins for molecular weight marker adopted are bovine serum albumin (m.w. 67,000), ovalbumin (m.w. 45,000), carbonic anhydrase (m.w. 29,000) and trypsin inhibitor (m.w. 20,100) respectively.

Since KYM-SF which is also a subject of this invention can grow without serum, t-PA can be collected in its single-chain form in the process of the present invention without being inferior in the quantity of production compared with conventional cell strains (see FIG. 2).

When collection of double-chain t-PA is desired, it can be obtained easily by culturing KYM-SF in a medium added with serum in such a small amount that would not be harmful in the purification or by adding a plasmin agarose column to the purification step and converting single-chain t-PA into double-chain t-PA. Such selectivity for the production of single-chain t-PA or double-chain t-PA is attributed to the growth characteristics of KYM-SF, and is not available unless KYM-SF is used.

For the production of t-PA, it is suitable to culture KYM-SF in a fermenter or the like and to replace the medium continuously after sufficient growth of cells or to replace a supernatant with a fresh at intervals of 1-4 days by the cell-sedimentation method so as to obtain a t-PA-containing medium continuously over about 3 months.

The purification of t-PA can be achieved by a combination of general purification methods for proteins such as adsorption, ion-exchange, gel filtration, and various affinity chromatographies. Among them, efficient purification is feasible by using a monoclonal antibody in affinity chromatography.

For example, the isolation and purification may be conducted in the following manner. A culture medium recovered is subjected to centrifugation to remove cells and other insoluble materials. The resulting supernatants are applied to a column of zinc chelating-agarose prepared by the method of Porath et al. [Nature, 258, 598-599 (1975)] and equilibrated with Tris-HCl (pH 7.4) containing NaCl and Tween 80 (trade name). The column is subjected to gradient elution with the above buffer (pH 7.4) containing the increasing concentration of imidazole. The t-PA enriched fractions eluted from the column are pooled and then applied to an immunoaffinity column which contains Sepharose 4B (trade name; product of Pharmacia AB) conjugated by the CNBr-activation method with an anti-t-PA monoclonal antibody obtained using KYM-SF-derived t-PA as antigen. After completion of the charging, t-PA is eluted with 2M of potassium thiocyanate and concentrated by ultrafiltration.

The concentrated solution of t-PA is developed by a column of "Sephacryl S-200" (trade name; product of Pharmacia AB). Active fractions are pooled again, thereby obtaining a purified t-PA sample. All the procedures described above are conducted at 4° C.

Besides the above method, the purification method reported by Collen et al. [J. Biol. Chem., 256, 7035-7041 (1981)] is also a well-known one.

The monoclonal antibody employed for the purification has the following characteristics.

(1) Conjugates specifically to t-PA derived from KYM-SF.

(2) Molecular weight: about 150,000.

(3) IgG subclass: IgG2a.

The monoclonal antibody is obtained as follows: For immunization, highly purified t-PA derived from KYM-SF is injected twice per 3 weeks into BALB/c mouse. The spleen cells taken out of the mouse are fused with mouse myeloma cells pretreated with colcemid as described by Miyahara et al. [Japanese Patent Application Laid-Open No. 52287/1986; Miyahara et al., Biochem. Biophys. Res. Commun. 124, 903 (1983)]. An established method with polyethylene glycol is adopted for the fusion of these cells [Kohler et al., Nature, 256, 495-497 (1975); R. A. Goldsberg et al., Nature, 267, 707 (1977); G. Galfre et al., Methods in Enzymology (J. J. Langone, H. Van Vunakis) 73, 3-46, Academic Press, New York (1981)]. The resulting hybridoma cells are distributed in the wells of a 96-well plate and cultured. Hybridoma cells capable of producing a single antibody specific to KYM-SF-derived t-PA are selected using an enzyme immunoassay (or monitoring antibody titers), and then purified using a limited dilution method.

Among t-PAs obtained in the above-described manner, t-PA produced by culturing KYM-SF in a serum-free medium is collected and purified as single-chain t-PA.

Structural verification of the t-PA can be effected by its electrophoretic analysis in an SDS-polyacrylamide gel under reducing conditions. Results of the test are shown in FIG. 2. As is apparent from FIG. 2, only single-chain molecules are detected with respect to t-PA produced by culturing KYM-SF in a serum-free medium.

The followings are physical and chemical properties of KYM-SF-derived single-chain t-PA obtained in the above-described manner.

(1) Molecular weight:

The molecular weight was estimated to be 60,000-73,000 in both reduced and unreduced states by an electrophoretic analysis in an SDS-polyacrylamide gel (FIG. 2).

(2) Isoelectric point: pH 6-8.

(3) Sequence of 10 amino acid residues from the N-terminal:

Single-chain t-PA was analyzed by Edman degradation for 10 cycles [Edman et al., European J. Biochem., 1 80 (1967)]. The resulting PTH-amino acids were analyzed and identified by high performance liquid chromatography. Results are shown in Table 1.

TABLE 1

| N-Terminal Amino Acid Sequence of Single-Chain t-PA Derived from KYM-SF | | | | | | | | | | |
|---|---|---|---|---|---|---|---|---|---|---|
| | 1 | 2 | 3 | 4 | 5 | 6 | 7 | 8 | 9 | 10 |
| Glycine terminal | Gly— | Ala— | Arg— | Ser— | Tyr— | Gln— | Val— | Ile— | X— | Arg— |
| Serine terminal | | | | Ser— | Tyr— | Gln— | Val— | Ile— | X— | Arg— |

| N-Terminal Amino Acid Sequence of Single-Chain t-PA Derived from Melanoma (Bowes Strain) [P. Wallen et al. Eur. J. Biochem., 132, 681 (1983)] | | | | | | | | | | |
|---|---|---|---|---|---|---|---|---|---|---|
| | 1 | 2 | 3 | 4 | 5 | 6 | 7 | 8 | 9 | 10 |
| Glycine terminal | Gly— | Ala— | Arg— | Ser— | Tyr— | Gln— | Val— | Ile— | Cys— | Arg— |
| Serine terminal | | | | Ser— | Tyr— | Gln— | Val— | Ile— | Cys— | Arg— |

Note:
X: Cysteine cannot be identified by an analysis which relies upon Edman degradation. However, X was supposed to be Cys from results of a sequence analysis on cDNA.
The abbreviations of amino acids have the following meanings:
Gly: glycine; Ala: alanine; Ser: serine; Tyr: tyrosine; Gln: glutamine; Val: valine; Ile: isoleucine.

From the above results, the single-chain t-PA obtained in accordance with the process of this invention has been confirmed to have the same amino acid sequence as the single-chain t-PA purified from the established cell line of human melanoma [P. Wallen et al., Eur. J. Biochem., 132, 681-686 (1983)]. Two amino acid sequences, one with the glycine (Gly) terminal and the other with the serine (Ser) terminal, are shown in the table, because the glycine terminal which is supposed to be the N-terminal of single-chain t-PA was probably subjected to processing to lose the three amino acids during the culturing and purification steps and as a result, appeared as the serine-terminal. Regarding the processing of the N-terminal of t-PA, exactly the same phenomenon has been reported on t-PA derived from the human melanoma [P. Wallen et al., Eur. J. Biochem., 132, 681-686 (1983)].

(4) Affinity to fibrin:

Substantially stronger affinity to fibrin has been observed compared with urokinase.

Further, the double-chain t-PA collected and purified in accordance with the process of this invention is not distinguishable from the t-PA purified from the established cell line of human melanoma. It has also been confirmed to be t-PA from other physical and chemical properties.

As has been described above, single-chain and/or double-chain t-PA can be produced very advantageously by using KYM-SF, mass-culturing the cell strain in a selected medium by the stirred suspension culturing method, and then collecting and purifying t-PA in a manner known per se in the art.

The present invention will hereinafter be described specifically by the following Example.

EXAMPLE

Production of t-PA by the serum-free culture of the human rhabdomyosarcoma variant KYM-SF:

(a) Activity measurement:

The measurement of t-PA activity was conducted by the fibrin clot lysis time method [Rijiken et al., Biochem. Biophys. Acta., 580 140 (1979)] with a modification as follows.

To prepare fibrin clots, the following solutions were each successively mixed and incubated for 2 minutes at 37° C.: 500 $\mu$l of 2.4 mg/ml human fibrinogen, 50 $\mu$l of 0.3 mg/ml human plasminogen, t-PA solution of adequate amount and 40 NIH units/ml thrombin, with each of them being diluted with and dissolved in 50 mM phosphate buffer (pH 7.75) containing 0.1M of NaCl and 0.25% of gelatin. A nylon ball with a diameter of 3.2 mm was then placed gently on the fibrin clots and the time was measured until the nylon ball reached the bottom of the test tube. On the other hand, a calibration curve was prepared using as a standard single-chain t-PA whose activity had been measured using WHO international standard t-PA (Lot. 83/517) by the above improved method of the fibrin clot lysis time method, and the activity of t-PA was expressed in terms of t-PA international unit (I.U.)

(b) Preparation of anti-t-PA monoclonal column:

(i) Purification of t-PA for the antigen:

Preparation of the monoclonal antibody was carried out by the method of Miyahara et al. [Japanese Patent Application Laid-Open No. 52287/1986; Miyahara et al., Biochem. Biophys. Res. Commun., 124, 903 (1983)]. Specifically, the following procedure was adopted.

For immunization, t-PA was purified from culture medium of KYM-SF by the conventional method of Rijken and Collen [J. Biol. Chem., 256, 7035-7041 (1981)]. Namely, a recovered medium which had been obtained by culturing the variant KYM-SF was subjected to a zinc chelating column in the above-described manner, whereby active fractions were obtained. The thus-obtained active fractions were combined in a dialysis tubing, to which powder of polyethylene glycol 20,000 (product of Wako Pure Chemical Industries, Ltd.) was sprinkled to concentrate the solution, which was then dialyzed for 24 hours against 0.01M phosphate buffer (pH 6.7). The dialyzate was applied to a concanavalin-A bound Sepharose column (1 cm across $\times$ 20 cm long; manufactured by Pharmacia AB) which had been equilibrated with 0.01M phosphate buffer (pH 6.7). After washing the column with the same buffer, the column was subjected to gradient elution with 0.01M phosphate buffer (pH 6.7) containing increasing concentration of potassium thiocyanate to 0.6M and of $\alpha$-methylmannoside to 3M. The active fractions eluted were put into a dialysis tubing which was then sprinkled with powder of polyethylene glycol 20,000, concentrated at 4° C., and then dialyzed for 24 hours against PBS buffer (pH 6.7). Precipitated active fractions were recovered by centrifugation (10,000$\times$g, 30 min) and dissolved completely in 0.01M phosphate buffer (pH 6.7) containing 0.6M potassium thiocyanate. The resulting solution was developed by a column of "Sephacryl S-200" (product of Pharmacia AB) which had been equilibrated with 0.01M phosphate buffer (pH 6.7) containing 0.6M potassium thiocyanate. The fractions containing t-PA (about 2 mg as proteins) were provided as an antigen for the preparation of the monoclonal antibody.

(ii) Method for the preparation of the monoclonal antibody:

A BALB/c mouse (7 weeks old, female) was intraperitoneally injected twice at an interval of 3 weeks with 0.2 ml of a solution which contained about 13 $\mu$g of purified t-PA and 0.1 ml of Freund complete adjuvant. Two weeks later, approximately 13 $\mu$g of purified t-PA was further injected intraperitoneally together with 0.37 mg of aluminum hydroxide. Three days later, spleen cells were obtained, 2.4$\times$10$^8$ cells of them were mixed with 2.4$\times$10$^7$ mouse myeloma cells (X63-Ag8-6.5.3.) which had been subjected to the colcemid treatment (50 ng/ml, 25 hours), and conventional cell fusion using polyethylene glycol was then conducted in the following manner [Kohler et al., Nature, 256, 495-497 (1975); R. A. Goldsberg et al., Nature, 267, 707 (1977); G. Galfre et al., Methods in Enzymology (J. J. Langone, H. Van Vunakis), 73, 3-46, Academic Press, New York (1981)].

Myeloma cells and spleen cells, both, in Eagle's medium were mixed at the above ratio, followed by centrifugation at 200$\times$g for 10 minutes. The resulting pellet was suspended in Eagle's medium warmed to 37° C., which contained 50% polyethylene glycol 4000 (product of Wako Pure Chemical Industries, Ltd.). The thus-prepared suspension was stirred for about 1 minute. One milliliter of Eagle's medium was added ten times at intervals of 30 seconds to a total amount of 10 ml, followed by centrifugation to remove the polyethylene glycol. The cells were resuspended in RPMI 1640 medium which contained 10% of fetal calf serum. About 140 $\mu$l of the suspension was distributed into the wells of a 96-well plate.

About 140 $\mu$l of HAT medium (hypoxanthine, aminopterin, thymidine containing medium) was added 24 hours later, and while replacing the medium every 2-3 days, the hybridoma cells were allowed to grow in the wells. Colonies producing a marked amount of antibody specific to the antigen in their culture supernatants as measured by a usual enzyme immunoassay were obtained. The colonies were then subjected one after another to cloning by the limited dilution analysis, whereby hybridoma cells capable of producing immunoglobulin (IgG2a) specific to t-PA were obtained.

Hybridoma cells ($1 \times 10^7$ cells) were inoculated to a BALB/c nude mouse which had been administered with 0.5 ml of pristane 7 days before and then allowed to grow in ascites. Two weeks later, the ascites was taken out, and centrifuged to collect an intermediate layer between an upper pristane layer and a cell pellet. The intermediate layer was salted out with 50% saturation of ammonium sulfate, followed by centrifugation to obtain a precipitate. The precipitate was dissolved in PBS buffer (pH 7.2) containing 0.15M of NaCl and dialyzed three times against 1 liter of the above buffer. The dialyzate was provided as an anti-t-PA monoclonal antibody immunoglobulin fraction (IgG2a).

An anti-t-PA monoclonal antibody was conjugated with Sepharose 4B (trade name; product of Pharmacia AB) with the CNBr-activation method as described by Miyahara et al. [Biochem. Biophys. Res. Commun., 124, 903 (1984)].

(c) Culture of KYM-SF and recovery of medium thereof:

Employed as a medium was RPMI-1640 medium (product of Nissui Chemical Industries, Ltd.) which contained, per liter, 90 mg of human transferrin ["No. T2252" (trade name); product of Sigma Corporation], 4.6 mg of monoethanolamine (product of Nakarai Chemicals, Ltd.), 13 μg of selenious acid (product of Nakarai Chemicals, Ltd.) and 1 g of bovine serum albumin "Fraction-V" (trade name; product of Armour Pharmaceutical Co., Ltd.).

KYM-SF cells (IFO 150135) were inoculated to a 25-cm$^2$ culture flask (manufactured by Corning Glass Works) and were cultured while replacing the whole volume of medium once every three days. When 30–60 ml of cell suspension was obtained after subculturing, suspension culture with stirring was started in a 100-ml glass flask fermenter.

The inoculation to the 100-ml fermenter was conducted at an inoculum size of at least $2 \times 10^5$ cells/ml. The cells were cultured with stirring under the following conditions: temperature; 37° C., pH range; 6.8–7.3, and surface aeration with 20 ml/min of a mixed gas of air and $CO_2$ in a proportion of 2.5% of the air. The replacement of the medium in the fermenter was effected by stopping the stirring every 2–3 days and replacing approximately 80% of the supernatant.

When the cell concentration reached $1.5-2.0 \times 10^6$ cells/ml 7 days later, the culturing was stopped. The thus-grown cells were transferred to a fivefold-capacity, namely, 500-ml fermenter and cultured under the same conditions except for the rate of aeration. As the rate of aeration to the 500-ml fermenter, surface aeration was performed at a rate of 100 ml/min with a mixed gas of air and $CO_2$ in a proportion of 2.5% of the air. The replacement of the medium was conducted every 2–3 days in a similar manner as for the above-described culture.

Thereafter, the fermenter size was increased successively by fivefold in capacity, namely, to 2.5 l and 12.5 l at intervals of 7–10 days under the same conditions except for the rate of aeration. The inoculum size in each stage was $3 \times 10^5$ cells/ml. The transfer of cells to the larger fermenter was conducted when the cell concentration reached $1.5-2.0 \times 10^6$ cells/ml upon an elapsed time of 7–10 days after the inoculation. As to the rate of aeration, a mixed gas composed of air and 2.5% of $CO_2$ was fed as surface aeration at a rate of 400 ml/min in the stage of the 2.5 l culture, and in the stage of the 12.5 l culture, air, $CO_2$, $O_2$ and mixed gases thereof were fed to control the pH within the range of 6.8–7.3 and $pO_2$ at 10% minimum. Replacement of the medium was conducted in a similar manner as for the 100-ml culture and 500-ml culture.

When the culture in the 12.5-l fermenter (manufactured by Shibata Scientific Technology Limited) reached $1.5-2.0 \times 10^6$ cells/ml, the scale-up was finished. The medium was replaced once every 1–2 days in the same manner as for the above-described medium replacements and was recovered. During that period, aeration was continued with air, $O_2$, $CO_2$ and mixed gases thereof so as to maintain pH within the range of 6.8–7.3 and $pO_2$ at 10% minimum.

Culture medium thus recovered was added with 0.01% Tween 80 and then combined and pooled as a recovered culture medium.

(d) Purification of t-PA:

The recovered culture medium was centrifuged at $10,000 \times g$ for 10 min in "Hitachi Refrigerated Centrifuge SCR 20BB" (trade name; manufactured by Hitachi, Ltd.), whereby insoluble materials such as cells and insoluble materials were removed and a supernatant was obtained.

A zinc chelating-agarose column (5 cm in diameter $\times$ 25.2 cm long), which had been prepared by the method of Porath et al. [Nature, 258, 598–599 (1975)], was equilibrated with 20 mM tris-HCl buffer (pH 7.4) containing 1M of NaCl and 0.01% of Tween 80 and was then loaded with the above-described supernatant.

The column was thereafter washed with the aforementioned equilibrating buffer, followed by gradient elution from the above buffer to the one containing 50 mM of imidazole, and t-PA active fractions were pooled.

The monoclonal antibody column (18 cm in diameter $\times$ 1 cm long) was equilibrated with 10 mM phosphate buffer (pH 7.2) containing 1M of NaCl, and was then loaded with the t-PA fractions eluted from a zinc chelating column. After completion of the loading, the column was washed with the same buffer and then eluted with the buffer containing 2M of potassium thiocyanate. Fractions containing t-PA were collected and then concentrated through an ultrafiltration membrane (exclusion molecular weight: 10,000; product of Amicon Inc.).

The concentrate of the active fractions was thereafter developed by a column of "Sephacryl S-200" (trade name; product of Pharmacia AB) which had been equilibrated with 1M $NH_3HCO_3$. Active fractions were pooled again to provide a purified t-PA sample. The purification procedures described above were all conducted at 4° C.

As has been described above, the purified sample of t-PA was obtained by the 4-step process.

Figure 3:
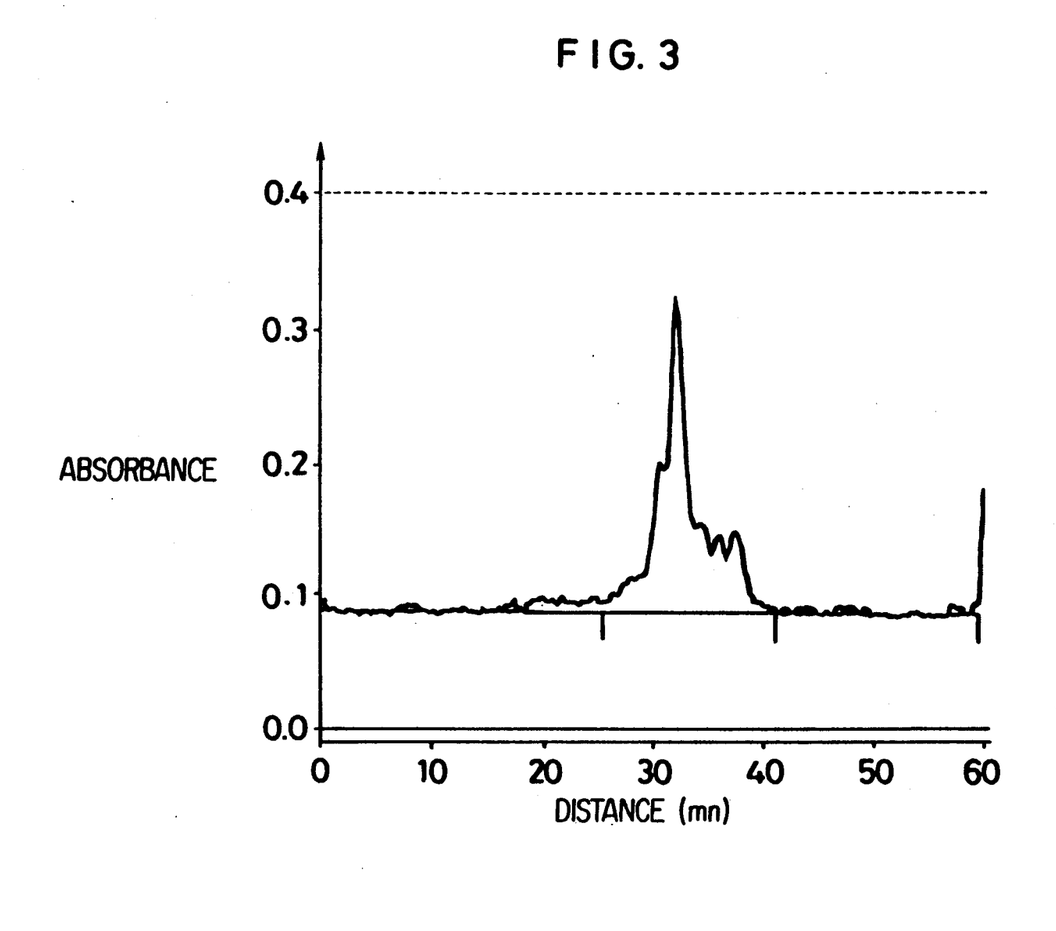
FIG. 3 depicts a densitometric tracing of purified single-chain t-PA separated in an electrophoresed gel.

The t-PA sample thus obtained was subjected to electrophoresis in an SDS gel containing 12.5% of polyacrylamide [Laemli et al., Nature, 227, 6808 (1970); Weber, K. et al., J. Biol. Chem., 244, 4406–4412 (1969)]. The gel was stained with Coomassie Brilliant Blue and its visible range absorption (660 nm) was measured by a densitometer "Ultrascan XL densitometer" (trade name; manufactured by LKB Corporation). As shown in FIG. 3, the purity was found to be at least 90%, thereby indicating a high degree of purification.

In addition, the t-PA thus purified showed a single band near 60,000-73,000 (FIG. 2) in both reduced and unreduced states when subjected to electrophoresis in an SDS gel containing 12.5% of polyacrylamide. The t-PA was hence found to be single-chain t-PA.

The purification fold in each stage of purification is shown in Table 2.

TABLE 2

|  | Total protein (mg) | Total enzyme activity (IU) | Specific activity (IU/mg) | Yield (%) | Purification fold |
|---|---|---|---|---|---|
| Supernatant of culture | 67,000 | 6,120,000 | 91.8 | 100 | 1 |
| Zinc chelating column | 1,100 | 3,590,000 | 3,260 | 59 | 35 |
| Monoclonal antibody column | 9.6 | 4,330,000 | 451,000 | 71 | 5,000 |
| Sephacryl S-200 | 8.8 | 4,220,000 | 480,000 | 69 | 5,300 |

In Table 2, each total enzyme activity indicates t-PA activity determined from a calibration curve which was obtained using WHO international standard t-PA (Lot. 83/517) in accordance with the improved method of the fibrin clot lysis method, each total protein was determined by the method of Lowry in which bovine serum albumin (product of Sigma Corporation) was used as a standard protein, and each specific activity is the corresponding total activity/total protein and indicates t-PA activity per mg. The purification folds indicate specific activities in the respective purification steps by allotting 1 to the degree of purification of the supernatant of the culture. Incidentally, the variations in total activity in the course of the purification seem to be attributable to influence due to the existence of materials inhibiting t-PA activity.

I claim:

1. A process for the production of human tissue plasminogen activator, which comprises culturing the human rhabdomyosarcoma-derived cell, KYM-SF, in a serum free medium which is substantially free of insulin and purification of single-chain and/or double-chain human tissue plasminogen activator from the medium.

2. The process as claimed in claim 1, wherein a monoclonal antibody which specifically binds human tissue plasminogen activator is used for the purification of human tissue plasminogen activator.

* * * * *

UNITED STATES PATENT AND TRADEMARK OFFICE
CERTIFICATE OF CORRECTION

PATENT NO. : 5,139,939

DATED : August 18, 1992

INVENTOR(S) : Akira Ohashi et al.

It is certified that error appears in the above-identified patent and that said Letters Patent is hereby corrected as shown below:

On the title page, item [75] inventor:
The third inventor's name is incorrect, should be, --Michinori Miyahara--.

Signed and Sealed this

Twenty-first Day of December, 1993

Attest:

BRUCE LEHMAN

*Attesting Officer*  *Commissioner of Patents and Trademarks*